United States Patent
Gordon et al.

(10) Patent No.: US 12,020,429 B2
(45) Date of Patent: Jun. 25, 2024

(54) IDENTIFYING CALCIFICATION LESIONS IN CONTRAST ENHANCED IMAGES

(71) Applicant: Nano-X AI Ltd., Shefayim (IL)

(72) Inventors: Ronen Marc Gordon, Tel Mond (IL); Amir Bar, Berkeley, CA (US); Raouf Muhamedrahimov, San Francisco, CA (US); Ayelet Akselrod-Ballin, Kiryat Ono (IL)

(73) Assignee: Nano-X AI Ltd., Shefayim (IL)

( * ) Notice: Subject to any disclaimer, the term of this patent is extended or adjusted under 35 U.S.C. 154(b) by 380 days.

(21) Appl. No.: 17/350,019

(22) Filed: Jun. 17, 2021

(65) Prior Publication Data
US 2022/0405915 A1    Dec. 22, 2022

(51) Int. Cl.
*G06T 7/00* (2017.01)
*G06T 7/10* (2017.01)
*G16H 30/20* (2018.01)
*G16H 50/30* (2018.01)

(52) U.S. Cl.
CPC .............. *G06T 7/0012* (2013.01); *G06T 7/10* (2017.01); *G16H 30/20* (2018.01); *G16H 50/30* (2018.01); *G06T 2207/10081* (2013.01); *G06T 2207/20081* (2013.01); *G06T 2207/20084* (2013.01); *G06T 2207/30096* (2013.01)

(58) Field of Classification Search
CPC ...................... G06T 7/0012; G06T 7/10; G06T 2207/10081; G06T 2207/20081; G06T 2207/20084; G06T 2207/30096; G06T 7/11; G06T 2207/20072; G06T 2207/20076; G06T 2207/30048; G06T 2207/30101; G16H 30/20; G16H 50/30; G16H 30/40; G16H 50/20
See application file for complete search history.

(56) References Cited

PUBLICATIONS

Yang et al., "Automatic coronary calcium scoring using noncontrast and contrast CT images", Medical Physics, vol. 43, Issue 5, May 2016 (Year: 2016).*

(Continued)

*Primary Examiner* — Qian Yang (57) ABSTRACT

There is provided a method of training a machine learning model, comprising: for each set of sample medical images depicting calcification within a target anatomical structure wherein each set includes non-contrast medical image(s) and contrast enhanced medical image(s), correlating between calcifications depicted in the target anatomical structure of the contrast enhanced image(s) with corresponding calcifications depicted in the target anatomical structure of the non-contrast medical image(s), computing calcification parameter(s) for calcification depicted in the respective target anatomical structure, labelling each contrast enhanced medical image with the calcification parameter(s), and training the machine learning model on a training dataset that includes the contrast enhanced medical images of the sets, each labelled with ground truth label of a respective calcification parameter(s), for generating an outcome indicative of a target calcification parameter(s) for calcification depicted in the target anatomical structure of a target contrast enhanced medical image provided as input.

15 Claims, 3 Drawing Sheets

(56) References Cited

PUBLICATIONS

Arad et al., "Treatment of Asymptomatic Adults With Elevated Coronary Calcium Scores With Atorvastatin, Vitamin C, and Vitamin E—The St. Francis Heart Study Randomized Clinical Trial", Journal of the American College of Cardiology, vol. 46, No. 1, 2005 (Year: 2005).*

Bischoff et al. "Cardiovascular Risk Assessment Based on the Quantification of Coronary Calcium in Contrast-Enhanced Coronary Computed Tomography Angiography", European Heart Journal—Cardiovscular Imaging, 13(6): 468-475, Published Online Dec. 13, 2011.

Korkinof et al. "High-Resolution Mammogram Synthesis Using Progressive Generative Adversarial Networks", ArXiv Preprint ArXiv:1807.03401v1, p. 1-19, Jul. 9, 2001.

Nadjiri et al. "Accuracy of Calcium Scoring Calculated From Constrast-Enhanced Coronary Computed Tomography Angiography Using A Dual-Layer Spectral CT: A Comparison of Calcium Scoring From Real and Virtual Non-Contrast Data", PLoS One, 13(12): e0208588-1-e0208588-12, Dec. 6, 2018.

Otton et al. "A Method for Coronary Artery Calcium Scoring Using Contrast-Enhanced Computed Tomography", Journal of Cardiovascular Computed Tomography, 6(1): 37-44, Published Online Nov. 20, 2011.

Pavitt et al. "Deriving Coronary Artery Calcium Scores From CT Coronary Angiography: A Proposed Algorithm for Evaluating Stable Chest Pain", The International Journal of Cardiovascular Imaging, 30(6): 1135-1143, Published Online May 6, 2014.

Tang et al. "Contrast Phase Classification With A Generative Adversarial Network", Proceedings of the SPIE Medical Imaging 2020: Image Processing, Houston, TX, USA, Mar. 10, 2020, 11313: 1-8, Mar. 10, 2020.

* cited by examiner

IDENTIFYING CALCIFICATION LESIONS IN CONTRAST ENHANCED IMAGES

FIELD AND BACKGROUND OF THE INVENTION

The present invention, in some embodiments thereof, relates to machine learning models and, more specifically, but not exclusively, to machine learning models for processing anatomical medical images.

Medical images may be captured during administration of contrast, such as intravenous contrast administration into the vasculature of the subject, and/or during non-administration of contrast. The contrast and/or non-contrast images may be used for visually delineating different anatomical features. For example, contrast enhanced images delineate blood vessels.

SUMMARY OF THE INVENTION

According to a first aspect, a computer-implemented method of training a machine learning (ML) model for identifying calcification in contrast enhanced medical images, comprises: for each set of a plurality of sets of sample medical images of a plurality of sample subjects depicting calcification within a target anatomical structure wherein each set includes at least one non-contrast medical image and at least one contrast enhanced medical image, correlating between calcifications depicted in the target anatomical structure of the at least one contrast enhanced image with corresponding calcifications depicted in the target anatomical structure of the at least one non-contrast medical image, computing at least one calcification parameter for calcification depicted in the respective target anatomical structure, labelling each contrast enhanced medical image with the at least one calcification parameter, and training the ML model on a training dataset that includes the plurality of contrast enhanced medical images of the plurality of sets, each labelled with ground truth label of a respective at least one calcification parameter, for generating an outcome indicative of a target at least one calcification parameter for calcification depicted in the target anatomical structure of a target contrast enhanced medical image provided as input.

According to a second aspect, a computer-implemented method of identifying at least one calcification parameter, comprises: feeding a target contrast enhanced medical image depicting a target anatomical structure into an ML model training on a training dataset of a plurality of contrast enhanced medical images each labelled with ground truth label of a respective at least one calcification parameter, and obtaining an outcome indicative of a target at least one calcification parameter for calcification depicted in the target anatomical structure from the ML model.

According to a third aspect, a computing device for training a machine learning (ML) model for identifying calcification, comprises: at least one hardware processor executing a code for: for each set of a plurality of sets of sample medical images of a plurality of sample subjects depicting calcification within a target anatomical structure wherein each set includes at least one non-contrast medical image and at least one contrast enhanced medical image, correlating between calcifications depicted in the target anatomical structure of the at least one contrast enhanced image with corresponding calcifications depicted in the target anatomical structure of the at least one non-contrast medical image, computing at least one calcification parameter for calcification depicted in the respective target anatomical structure, labelling each contrast enhanced medical image with the at least one calcification parameter, and training the ML model on a training dataset that includes the plurality of contrast enhanced medical images of the plurality of sets, each labelled with ground truth label of a respective at least one calcification parameter, for generating an outcome indicative of a target at least one calcification parameter for calcification depicted in the target anatomical structure of a target contrast enhanced medical image provided as input.

In a further implementation form of the first, second, and third aspects, correlating comprises: registering between the target anatomical structure depicted in the at least one non-contrast medical image and the same corresponding target anatomical structure depicted in the at least one contrast enhanced medical image, segmenting calcification depicted in each respective non-contrast image, computing masks for respective segmented calcification of respective non-contrast images, and overlaying respective masks on the corresponding contrast images for delineating calcification depicted therein.

In a further implementation form of the first, second, and third aspects, further comprising: training a coarse-to-fine ML model on a training dataset that includes coarse masks overlaid on the contrast images each labeled with a ground truth of a corresponding fine mask obtained from the segmentation of the non-contrast images, wherein the coarse-to-fine ML model generates an outcome of a fine masks (to be applied to the contrast image) in response to an input of a coarse mask, and feeding the respective mask into the coarse-to-fine ML model to obtain a fine mask, and placing the fine mask on the contrast image.

In a further implementation form of the first, second, and third aspects, the training dataset further comprises the masks computed for the contrast images, and wherein the ML model is further trained for generating a target segmentation delineating calcification for the target contrast enhanced medical image.

In a further implementation form of the first, second, and third aspects, training the ML model comprises: training a baseline ML model on a baseline training dataset that includes the plurality of non-contrast medical images of the plurality of sets, each labelled with the ground truth label of the respective at least one calcification parameter determined for the respective non-contrast medical image, wherein training the ML model comprises further training the baseline ML model on the training dataset that includes the plurality of contrast enhanced medical images of the plurality of sets, each labelled with ground truth label of the respective at least one calcification parameter determined for the corresponding non-contrast medical image.

In a further implementation form of the first, second, and third aspects, further comprising: accessing a plurality of accessory non-contrast medical images without corresponding contrast enhanced medical images, determining, for each accessory non-contrast medical image, at least one calcification parameter for the respective calcification depicted in the target anatomical structure, synthesizing at least one contrast medical image from each accessory non-contrast medical image, labelling each synthesized contrast medical image with the ground truth label of the at least one calcification parameter determined for the non-contrast medical image used for synthesis of the synthesized contrast medical image, and including a plurality of labelled synthesized contrast medical images in the training dataset used for training the ML model.

In a further implementation form of the first, second, and third aspects, further comprising analyzing the at least one contrast enhanced medical image to determine at least one specific contrast phase, and selecting contrast enhanced medical images designed as the at least one specific contrast phase, and excluding contrast enhanced medical images depicted non-selected contrast phases from further processing.

In a further implementation form of the first, second, and third aspects, further comprising excluding non-contrast medical images from the training dataset.

In a further implementation form of the first, second, and third aspects, the ML model is implemented as a neural network based regression model.

In a further implementation form of the first, second, and third aspects, wherein the medical image includes slices extracted from a CT scan.

In a further implementation form of the first, second, and third aspects, the contrast enhanced image comprises a contrast-enhanced coronary computed tomography (CT) angiography (CTA) image, the non-contrast enhanced image comprises a non-contrast enhanced CT image, the target anatomical structure comprises a coronary artery, and the at least one calcification parameter comprises a coronary artery calcification (CAC) score and/or class and/or Agatston score and/or risk category.

In a further implementation form of the first, second, and third aspects, further comprising: accessing, for each contrast enhance image, at least one image parameter, creating a plurality of records, each record including a respective contrast enhanced image, the respective at least one image parameter, and the ground truth label of the respective at least one calcification parameter, and including the plurality of records in the training dataset used to train the ML model.

In a further implementation form of the first, second, and third aspects, the at least one image parameter is selected from a group consisting of: kernel reconstruction, dose, scan protocol, single source vs dual source, ECG obtained during image acquisition, heart rate during image acquisition, administration of vasodilator prior to image acquisition, DICOM metadata, slice thickness, and increment.

In a further implementation form of the first, second, and third aspects, further comprising: accessing, for each contrast enhance image, at least one subject parameter, creating a plurality of records, each record including a respective contrast enhanced image, the respective at least one subject parameter, and the ground truth label of the respective at least one calcification parameter, and including the plurality of records in the training dataset used to train the ML model.

In a further implementation form of the first, second, and third aspects, the at least one subject parameter is selected from a group consisting of: a subject demographic parameter, a medical history parameter, smoking history, family history, diabetes history, chronic kidney disease history, blood test values, cholesterol values, a previous calcification parameter, and age over a threshold.

In a further implementation form of the first, second, and third aspects, the contrast enhanced image comprises a CTA image, the target anatomical structure comprises a coronary artery, and the at least one calcification parameter comprises a CAC score and/or class and/or Agatston score and/or risk category.

In a further implementation form of the first, second, and third aspects, further comprising diagnosing heart disease when the CAC score and/or class and/or Agatston score and/or risk category is above a threshold.

In a further implementation form of the first, second, and third aspects, further comprising treating the subject for a treatment effective for preventing and/or reducing likelihood of heart disease when the CAC score and/or class and/or Agatston score and/or risk category is above a threshold, the treatment selected from a group consisting of: weight loss, exercise regimen, change in diet, and cholesterol lowering medication.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

The present invention, in some embodiments thereof, relates to machine learning models and, more specifically, but not exclusively, to machine learning models for processing anatomical medical images.

An aspect of some embodiments of the present invention relates to systems, methods, an apparatus, and/or code instructions (i.e., stored on a memory and executable by one or more hardware processors) for training a machine learning (ML) model for generating an outcome of one or more calcification parameters for calcifications (e.g., lesions) depicted in contrast enhanced medical images. Arterial calcifications are associated with increased cardiovascular risk. Identification and/or quantification of calcifications may be used, for example, for evaluation, diagnosis, and/or treatment of subjects. However, calcifications are difficult to identify visually in contrast enhanced medical images, since the contrast in the lumen appears very similar to calcifications in the wall of the lumen. Sets of medical images of sample subjects depicting a target anatomical structure are accessed. Each set includes non-contrast medical image(s) and contrast enhanced medical image(s), for example, CT scans with administered intravenous (IV) contrast, depicting the target structures of coronary arteries. Each pair of non-contrast and contrast medical images may be of the same subject, obtained during the same imaging session, such as during a CT scan protocol. One or more calcification parameters are determined for calcifications (e.g., lesions) depicted within the target anatomical structure, for example, for calcification within the coronary artery, a coronary artery calcification (CAC) score, and/or class and/or Agatston score and/or risk category may be computed. Other additional parameters may be obtained, for example, image parameters associated with the image such as settings of the CT machine and/or parameters of the administered radiation, and/or subject parameters associated with the respective subject such as medical history and/or demographics. A training dataset is created, that includes the contrast enhanced medical images labelled with respective calcification parameter(s) and optionally labelled with the additional parameter(s). The ML model is trained on the training dataset for generating an outcome indicative of a target at least one calcification parameter for calcifications (e.g., lesions) depicted in the target anatomical structure of a target contrast enhanced medical image provided as input.

Optionally, virtual contrast enhanced medical images are synthesized from non-contrast enhanced medical images, such as when no corresponding contrast enhanced medical images are available. The virtual contrast enhanced medical images depict contrast within the target anatomical structure and depict the presence of calcification within the target anatomical structure when calcification is depicted in the non-contrast medical image.

At least some implementations of the systems, methods, apparatus, and/or code instructions described herein address the technical problem of identifying calcification lesions and/or computing calcification parameter(s) for the calcifications, within lumens depicted in contrast enhanced images, i.e., where contrast is present in the same lumen as the calcification, for example, coronary artery calcification when the coronary artery has contrast within. At least some implementations of the systems, methods, apparatus, and/or code instructions described herein improve the technology of machine learning, by providing a machine learning model that identifies calcification and/or computes calcification parameter(s) for the calcifications in anatomical structures (e.g., arteries) depicted in contrast enhanced images.

Calcification may occur in different blood vessels of the body. Calcification in arteries is associated with increased cardiovascular risk. The extent of coronary artery calcification (CAC) has been shown to be a strong and independent predictor for cardiovascular events. Usually, CAC scoring is performed in non-contrast-enhanced computed tomography (CT) examinations.

Traditionally, calcification is manually visually identified by radiologists in non-contrast enhanced image, since in contrast enhanced images, the presence of the white contrast in the lumen of the artery makes it difficult to distinguish the also white appearing calcification in the inner wall of the lumen. In many cases contrast enhanced images are preferred, since a diagnosis may be made by the radiologist using the contrast enhanced images without necessarily requiring the non-contrast enhanced images. For example, non-contrast enhanced scans do not allow for detection of coronary artery stenosis or non-calcified plaques, and therefore contrast enhanced scans are preferred. As such, the contrast enhanced images may be the only ones available. In cases where traditionally two sets of images are obtained, i.e., contrast enhanced images and non-contrast enhanced images, such as of the coronary arteries, the non-contrast enhanced images may be avoided by using the contrast enhanced images to detect calcification using at least some implementations, as described herein. Deriving all the information from a single enhanced enhance scan significantly reduces the radiation dose to the subject. Obtaining another set of non-contrast enhanced images increases radiation exposure to the subject and/or increases the workload of the radiologist reading two sets of images.

At least some implementations of the systems, methods, apparatus, and/or code instructions described herein improve over other approaches that attempted to identify calcification in contrast enhanced images. Such approaches used a set of rules, which were computed based on parameters of the images themselves. As such, the set of rules was successful on a small set of patients, but failed when tested in the wild, since the set of rules cannot be applied to the general case. In another prior approach, an empiric conversion factor was derived to convert a measured small voxel contrast-enhanced calcium volume (>320 HU in major coronary vessels) to an Agatston calcium score. However, this approach is limited to specific CT scanner models and/or specific analysis software, and cannot be generalized. In yet another approach, a spectral CT scanner using a dual-layer detector system is used. After absorption of the lower energetic photons in the top layer, the bottom layer detects a hardened spectrum of the same emitted radiation resulting in detection of two different energy spectra without temporal offset. Both spectra are detected simultaneously and with the same amount of radiation exposure. CACS was computed from the virtual non-contrast CT images computed from simultaneously acquired spectral data in comparison to standard non-contrast imaging. However, this approach is limited to specific CT scanners and cannot be generalized. The improvement provided by at least some implementations described herein is in using a machine learning model, trained on a training dataset of contrast enhanced images using corresponding non-contrast enhanced images as ground truth, optionally with one or more additional parameters, as described herein. The trained machine learning model identifies calcification in contrast enhanced images and/or computes calcification parameters for calcification depicted therein, for a wide set of different images captured under different conditions for different subjects, much wider than would be possible using a set of rules.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 1:
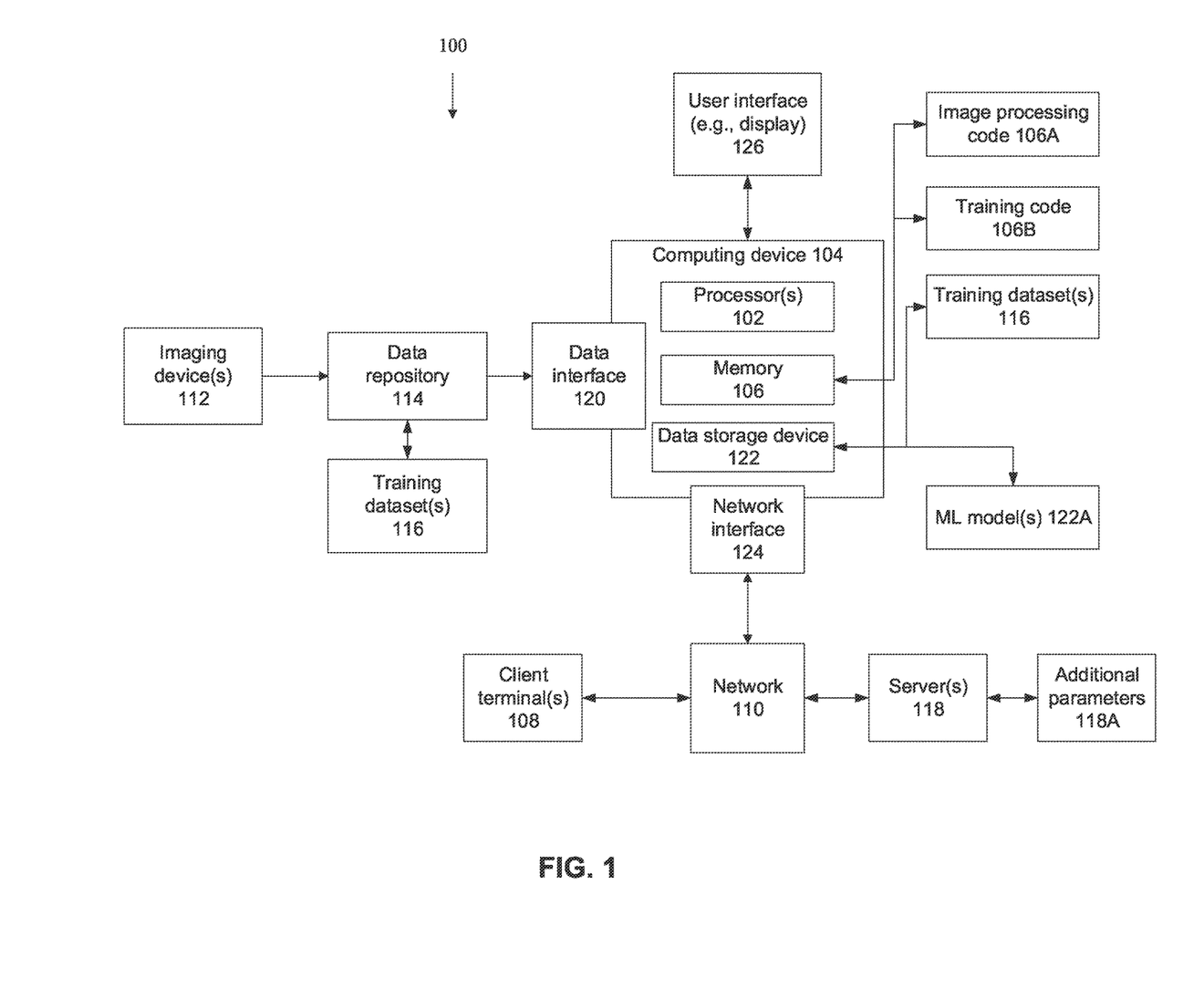
FIG. 1 is a block diagram of a system for training a machine learning model for computing calcification parameter(s) for calcifications depicted in contrast enhanced medical images and/or for training of the machine learning model, in accordance with some embodiments of the present invention.
Figure 2:
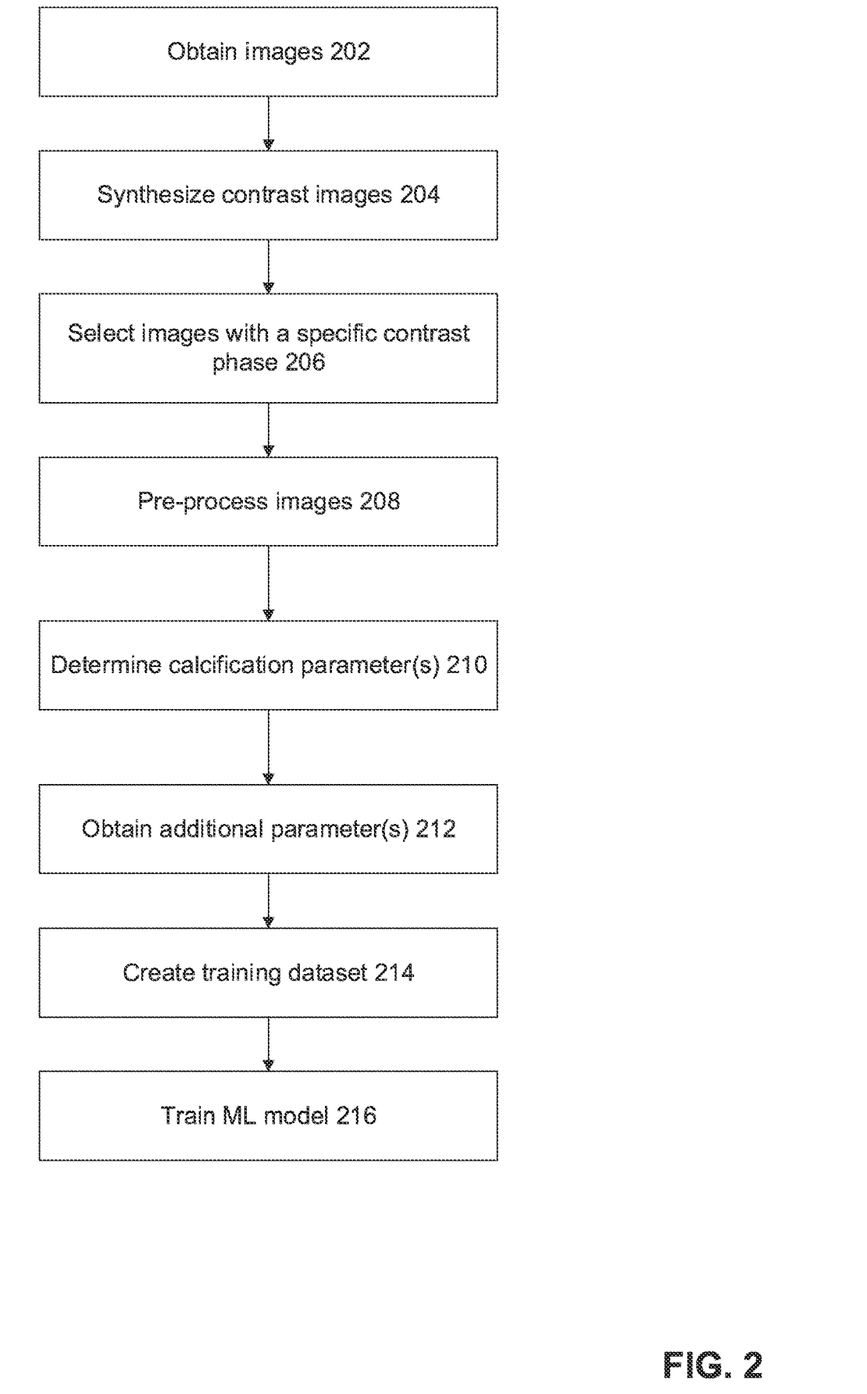
FIG. 2 is a flowchart of a method of training a machine learning model for computing calcification parameter(s) for calcifications depicted in contrast enhanced medical images, in accordance with some embodiments of the present invention.
Figure 3:
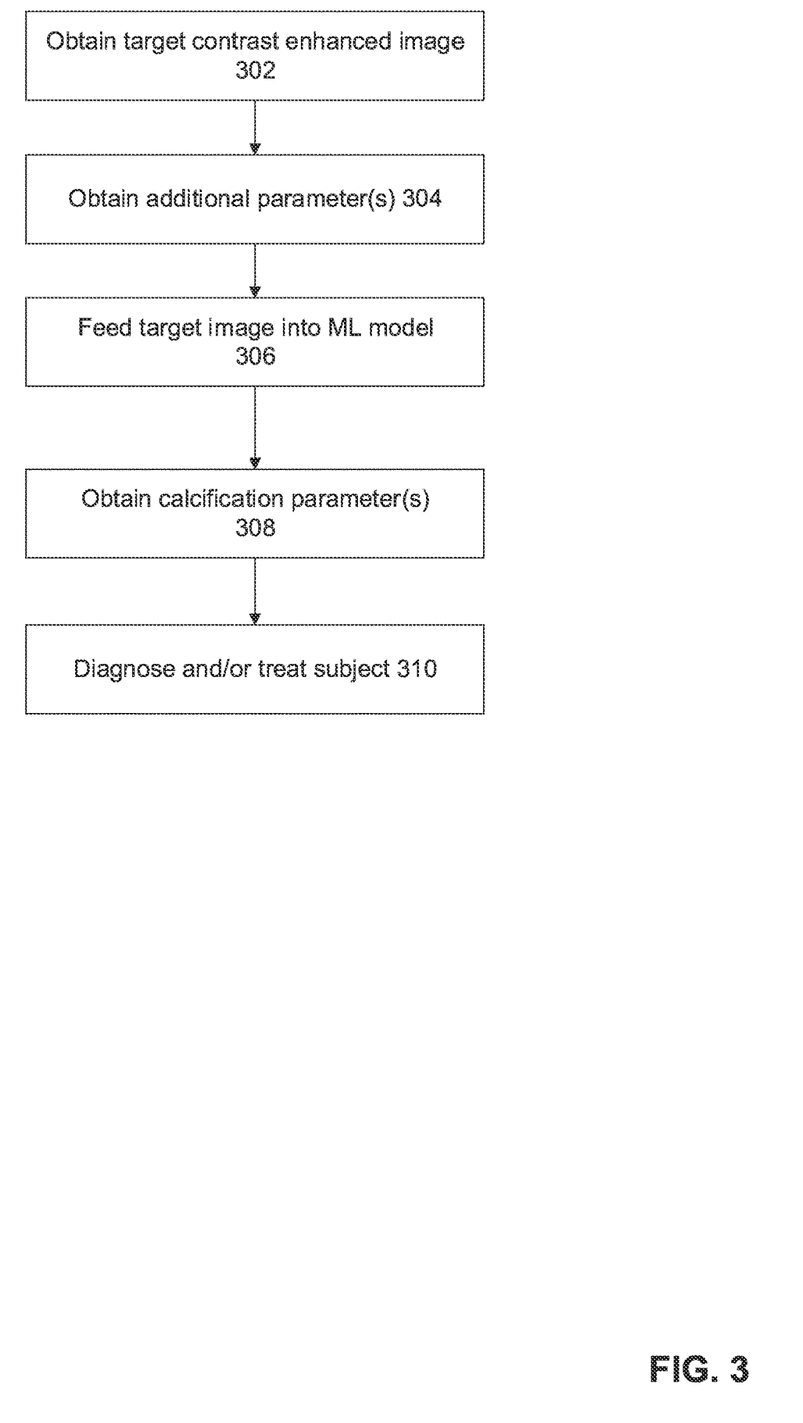
FIG. 3, which is a flowchart of a method of obtaining calcification parameter(s) for calcifications depicted in contrast enhanced medical images using the trained ML model, in accordance with some embodiments of the present invention.

Reference is now made to FIG. 1, which is a block diagram of a system 100 for training a machine learning model for computing calcification parameter(s) for calcifications depicted in contrast enhanced medical images and/or for training of the machine learning model, in accordance with some embodiments of the present invention. Reference is also made to FIG. 2, which is a flowchart of a method of training a machine learning model for computing calcification parameter(s) for calcifications depicted in contrast enhanced medical images, in accordance with some embodiments of the present invention. Reference is also made to FIG. 3, which is a flowchart of a method of obtaining calcification parameter(s) for calcifications depicted in contrast enhanced medical images using the trained ML model, in accordance with some embodiments of the present invention.

System 100 may implement the acts of the method described with reference to FIGS. 2-3, optionally by a hardware processor(s) 102 of a computing device 104 executing code instructions stored in a memory 106.

Computing device 104 may be implemented as, for example, a client terminal, a server, a virtual server, a radiology workstation, a virtual machine, a computing cloud, a mobile device, a desktop computer, a thin client, a Smartphone, a Tablet computer, a laptop computer, a wearable computer, glasses computer, and a watch computer. Computing 104 may include an advanced visualization workstation that sometimes is add-on to a radiology workstation and/or other devices for presenting indications of the identified calcification and/or other computer added detections to the radiologist.

Computing device 104 may include locally stored software that performs one or more of the acts described with reference to FIGS. 2-3, and/or may act as one or more servers (e.g., network server, web server, a computing cloud, virtual server) that provide services (e.g., one or more of the acts described with reference to FIGS. 2-3) to one or more client terminals 108 (e.g., remotely located radiology workstations, remote picture archiving and communication system (PACS) server, remote electronic medical record (EMR) server) over a network 110, for example, providing software as a service (SaaS) to the client terminal(s) 108, providing an application for local download to the client terminal(s) 108, as an add-on to a web browser and/or a medical imaging viewer application, and/or providing functions using a remote access session to the client terminals 108, such as through a web browser.

Different architectures based on system 100 may be implemented. In one example, computing device 104 provides centralized services. Training of the ML model 122A is performed centrally by computing device 104, as described herein. Inference may be centrally performed by computing device 104. Alternatively, training is performed by another computing device, and inference is centrally performed by computing device 104. Images may be provided to computing device 104 for centralized inference by the trained ML model(s) 122A. Images may be provided to computing device 104, for example, via an API, a local application, and/or transmitted using a suitable transmission protocol. The outcome of the inference may be provided, for example, to client terminal(s) 108 for presentation on a display and/or local storage, entered as a field in a medical record of the subject (e.g., calcification parameter automatically entered into a radiology report) stored by a medical record server, stored by computing device 104 and/or used as input into another process. In another example, computing device 104 provides centralized training of the ML model(s) 122A, using different training datasets provided by different client terminals 108 and/or servers 118. For example, training datasets originating from different hospitals, and/or training dataset for different imaging modalities, and/or for different body regions. Respective generated ML model(s) may be provided to the corresponding remote devices (e.g., client terminal(s) 108 and/or server(s) 118) for local use. For example, each hospital uses the ML model(s) created from their own training dataset for evaluation of new images captured at the respective hospital, and/or different ML model(s) are locally used to evaluate different medical images generated by different imaging modalities, such as fluoroscopy, voiding studies, and CT scans.

Imaging device 112 provides images, which may be included in training dataset(s) 116 optionally associated with one or more additional parameters 118A (e.g., as described herein) (e.g., stored on a PACS implementation of server 118), and/or provided for inference. Image device 112 captures one or more contrast enhanced images, for example, a 2D, 3D, and/or 4D imaging device, for example, CT contrast enhanced images (e.g., depicting coronary arteries, aorta, and/or other blood vessels), and fluoroscopic images depicting contrast injected into blood vessels, for example, injected intravenous (IV) contrast. 3D images, and/or slices of 3D images, and/or 4D images may be converted to 2D images for training and/or inference, for example, by selecting 2D slices from a 3D scan, and/or converting the 3D image into a 2D image such as by maximum pixel intensity (MPI) approaches. Alternatively, volumes may be used for training and/or inference, for example, multiple sequential CT slices. Inference and/or training may be performed on 3D volumetric data.

Training dataset(s) 116 of contrast enhanced and non-contrast medical images optionally including one or more additional parameters 118A (e.g., the additional parameters may be extracted from imaging device 112 and/or server 118 and/or from a medical record of the subject) may be stored in a data repository 114, for example, a storage server, a computing cloud, virtual memory, and a hard disk. Training dataset(s) 116 are used to train the ML model(s) 122A, as described herein. It is noted that training dataset(s) 116 may be stored by a server 118, accessibly by computing device 104 over network 110.

Computing device 104 may receive the training dataset(s) 116 (e.g., from data repository 114) and/or obtain images (e.g., from imaging device 112 and/or data repository 114) and/or obtain additional parameter(s) 118A of the images, using one or more data interfaces 120, for example, a wire connection (e.g., physical port), a wireless connection (e.g., antenna), a local bus, a port for connection of a data storage device, a network interface card, other physical interface implementations, and/or virtual interfaces (e.g., software interface, virtual private network (VPN) connection, application programming interface (API), software development kit (SDK)).

Hardware processor(s) 102 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 102 may include one or more processors (homogenous or heterogeneous), which may be arranged for parallel processing, as clusters and/or as one or more multi core processing units.

Memory 106 (also referred to herein as a program store, and/or data storage device) stores code instruction for execution by hardware processor(s) 102, for example, a random access memory (RAM), read-only memory (ROM), and/or a storage device, for example, non-volatile memory, magnetic media, semiconductor memory devices, hard drive, removable storage, and optical media (e.g., DVD, CD-ROM). For example, memory 106 may store image processing code 106A and/or training code 106B that implement one or more acts and/or features of the method described with reference to FIGS. 2-3.

Computing device 104 may include a data storage device 122 for storing data, for example, ML model(s) 122A and/or training dataset(s) 116. Data storage device 122 may be implemented as, for example, a memory, a local hard-drive, a removable storage device, an optical disk, a storage device, and/or as a remote server and/or computing cloud (e.g., accessed over network 110). It is noted that ML model(s) 122A and/or training dataset(s) 116 may be stored in data storage device 122, with executing portions loaded into memory 106 for execution by processor(s) 102.

ML model(s) 122A described herein may be implemented, for example, as a detector architecture, a classifier architecture, and/or a pipeline combination of detector(s) and/or classifier(s), for example, statistical classifiers and/or other statistical models, neural networks of various architectures (e.g., convolutional, fully connected, deep, encoder-decoder, recurrent, graph), support vector machines (SVM), logistic regression, k-nearest neighbor, decision trees, boosting, random forest, a regressor, and/or any other commercial or open source package allowing regression, classification, dimensional reduction, supervised, unsupervised, semi-supervised or reinforcement learning. Machine learning models may be trained using supervised approaches and/or unsupervised approaches.

Computing device 104 may include a network interface 124 for connecting to network 110, for example, one or more of, a network interface card, a wireless interface to connect to a wireless network, a physical interface for connecting to a cable for network connectivity, a virtual interface implemented in software, network communication software providing higher layers of network connectivity, and/or other implementations. Computing device 104 may access one or more remote servers 118 using network 110, for example, to obtain images and/or additional parameter(s) 118A to create the training dataset 116 and/or for inference, to obtain and/or provide training dataset(s) 116, an updated version of image processing code 106A, training code 106B, and/or the trained ML model(s) 122A.

It is noted that data interface 120 and network interface 124 may exist as two independent interfaces (e.g., two network ports), as two virtual interfaces on a common physical interface (e.g., virtual networks on a common network port), and/or integrated into a single interface (e.g., network interface). Computing device 104 may communicate using network 110 (or another communication channel, such as through a direct link (e.g., cable, wireless) and/or indirect link (e.g., via an intermediary computing device such as a server, and/or via a storage device) with one or more of:

Client terminal(s) 108, for example, when computing device 104 acts as a server providing image analysis services (e.g., SaaS) to remote radiology terminals, for analyzing remotely obtained anatomical images using the trained ML model(s) 122A.

Server 118, for example, implemented in association with a PACS, which may store training dataset(s) 116 and/or may store captured images for inference and/or store additional parameter(s) 118A.

Imaging device 112 and/or data repository 114 that store images acquired by imaging device 112. The acquired images may be fed into trained ML model(s) 122A for inference thereof, optionally with one or more additional parameters 118A as described herein, and/or used for generating training dataset(s) 116.

Computing device 104 and/or client terminal(s) 108 and/or server(s) 118 include and/or are in communication with a user interface(s) 126 that includes a mechanism designed for a user to enter data (e.g., subject data) and/or view the outcome of the inference of the captured image(s), such as the determined calcification parameter(s). Exemplary user interfaces 126 include, for example, one or more of, a touchscreen, a display, a keyboard, a mouse, and voice activated software using speakers and microphone.

Referring now back to FIG. 2, at 202, sets of sample medical images of sample subjects depicting a target anatomical structure is obtained. Target anatomical structures may be lumens in which calcification may be present and in which administered contrast may be present. Exemplary target anatomical structures include: vascular structures, arteries such as coronary arteries, aorta, carotid arteries, and renal arteries, heart valves, kidney, bladder, and gallbladder.

Each set includes one or more non-contrast medical images and one or more contrast enhanced medical images, optionally arranged as pairs, including a contrast images and a respective non-contrast image. The contrast and non-contrast medical images depict the same target anatomical structure, for example, captured at different contrast phases according to a standard protocol. Each pair of contrast and non-contrast medical images may be of the same subject, and may be obtained during the same study session, i.e., same imaging session, for example, where first a non-contrast CT scan is obtained followed by administration of IV contrast, and then a second contrast CT scan is performed.

Optionally, the medical images are captured by a radiation based imaging modality, for example, CT scans captured by a CT machine, fluoroscopy images, and/or x-ray images, such as chest x-rays, and/or voiding studies.

Optionally, the contrast enhanced image is a contrast-enhanced coronary computed tomography (CT) angiography (CTA) image, and the non-contrast enhanced image is a non-contrast enhanced CT image. The target anatomical structure is a coronary artery.

Medical images for the same type of target anatomical structure in different sample subjects may be obtained from a same type of imaging modality, with different settings, for example, different CT machines from different manufacturers, different models of CT machine, different imaging capture parameters, and different image capture protocols. The different settings may be used to obtain a broad ML model that may be used for inference for images captured by different imaging modalities and/or using different settings, rather than for specific machines and/or for specific settings. Alternatively, medical images may be specifically selected, for example, to create a customized ML model, for example, for a specific imaging machine, and/or for a specific imaging facility.

Medical images may be, for example, a single 2D slice (e.g., of a 3D CT scan), a sequence of 2D slices (e.g. of a CT scan), and/or 3D volumetric data (e.g., a 3D CT scan).

At 204, contrast images may be synthesized, such as when there are non-contrast medical images without corresponding contrast enhanced medical images. The contrast images corresponding to the non-contrast images may be synthesized. The synthesized images may depict calcification, or may not depict calcification, depending on the presence or absence of calcification in the corresponding non-contrast image.

It is noted that generating synthetic images that depict contrast and also depict calcification in the same lumen is technically challenging, since the contrast and calcification appear similar, and the synthesis is to be performed in a manner than enables a trained ML model to compute the calcification parameters for the calcification and/or to distinguish the calcification from the contrast.

In another implementation, non-contrast medical images may be synthesized, such as when there are contrast medical images without corresponding non-contrast enhanced medical images. The non-contrast images corresponding to the contrast images may be synthesized. The synthesized images may depict calcification, or may not depict calcification, depending on the presence or absence of calcification in the corresponding contrast image.

It is noted that generating synthetic images that depict calcification but exclude contrast, from contrast images that depict both calcification and contrast in the same lumen is technically challenging, since the contrast and calcification appear similar, and the synthesis is to be performed in a manner that correctly removes only the contrast but maintains the calcification to enable a trained ML model to compute the calcification parameters for the calcification and/or to distinguish the calcification from the contrast.

Synthesis approaches may include, for example, training and using a generative adversarial network (GAN) that includes a generative network that is trained to generate synthetic images that cannot be distinguished from real images by a discriminative network.

In an example, the exemplary process for synthesizing virtual contrast images from non-contrast images is based on Yucheng Tang et al., "*Contrast Phase Classification with a Generative Adversarial Network*", arXiv:1911.06395, incorporated herein by reference in its entirety, where the gated process produces a virtual non-contrast scan, matching a contrast scan in a selected phase, for example, arterial, portal venous, delayed, and the like.

At 206, images with a specific contrast phase may be selected.

Optionally, respective contrast enhanced medical image (s) are analyze to determine a respective contrast phase. The contrast phase depicted in the respective contrast enhanced medical image may be determined, for example, by extracting the contrast phase from metadata associated with the scan, and/or by a trained ML model that outputs an indication of the contrast phase. Optionally, contrast enhanced medical images designed one or more specific phases (e.g., arterial, portal venous, delayed) may be selected for including in a training dataset, along with the corresponding non-contrast enhanced image. Other contrast enhanced medical images of non-selected phases may be excluded from the training dataset along with the corresponding non-contrast enhanced image. For example, the arterial phase may be selected for vascular structures, such as coronary arteries and/or aorta. Other contrast phases may be selected for other anatomical structures, such as non-vascular anatomical structures, for example, for the bladder and/or kidney.

Some examples are now provided. Routine Chest with contrast scans are generally done at a scan delay of 55-70 seconds following administration of contrast to allow for optimal enhancement of soft tissues in the chest. When the Chest CT is done together with the Abdomen & Pelvis there are two common protocols for timing the contrast: the first one involves single delayed acquisition of chest, abdomen and pelvis. The other one uses two separate acquisitions—an earlier acquisition for chest (20-35 sec delay) and a second delayed acquisition for abdomen and pelvis in portal venous phase (70-80 sec delay). On CT Angiography (of coronary artery, aorta, or pulmonary arteries) the delay is much shorter (<10 sec) with Bolus Trigger set for HU of ROI. Routine chest CT contrast injection iodine concentration of 300-350 mgI/ml suffices whereas for CT angiography protocols, a higher concentration of 350-400 mgI/ml is preferred.

At 208, images may be pre-processed to enable automated computation of the calcification parameter(s).

It is noted that in some implementations, the pre-processing may be performed before selection of images with specific contrast phases described with reference to 206 of FIG. 2. For example, pre-filtering of images (e.g., based on DICOM metadata) and/or feature localization (e.g., heart localization) described herein may be performed prior to selection of images with specific contrast phases. Alternatively, first images with specific contrast phases are selected as described with reference to 206 of FIG. 2, and the pre-processing is then performed on the selected specific contrast images.

Optionally, images are pre-filtered, for example, using DICOM metadata. The pre-filtering may be performed, for example, using a set of rules applied to the DICOM metadata, such as to select CT chest images, and the like.

Optionally, the target anatomical structure, and/or another anatomical structure that includes the target anatomical structure and/or is in reference to the target anatomical structure is localized. For example, the heart may be localized, where the target of coronary arteries is located within the heart, and/or where the target of the ascending aorta is connected to the heart. The localization may be performed, for example, using segmentation code and/or localization code, such as using a machine learning model (e.g., neural network or other ML model implementation described herein) trained to localize the heart on a training dataset of images labelled with ground truth indications of the heart.

Calcifications depicted in the target anatomical structure of the contrast enhanced image may be correlated with corresponding calcifications depicted in the target anatomical structure of the non-contrast medical image. The calcifications may be identified, for example, by registration, segmentation, and/or computation of masks, for example, using the following exemplary process of one or more features.

Registration is performed between the non-contrast medical image and the contrast enhanced medical image of each set, optionally pairs of contrast and non-contrast images of the same subject during the same study (e.g., same imaging session). Registration may be at least between the respective target anatomical structures where calcifications are expected depicted in the non-contrast medical image and the contrast enhanced medical image of each set.

Segmentation of calcification is performed on the non-contrast image. Segmentation may be performed, for example, by segmentation code that selects pixels of certain value, and/or by a trained segmentation ML model. The segmentation ML model may be trained on a training dataset of non-contrast images labelled with segmentations of calcifications which may be manually performed by users.

Candidate masks for respective calcification lesions are computed according to the segmentation of the respective calcifications.

The candidate calcification segmentation mask, which may be coarse, is overlaid on the corresponding registered contrast image.

The coarse mask, which is overlaid on the contrast image, may be converted to a fine mask, which better delineates the outlines of the calcification depicted therein. The fine mask may be computed, for example, by a coarse-to-fine ML model. The coarse-to-fine ML model may be trained on a training dataset that includes the coarse masks each labeled with a ground truth of a corresponding fine mask obtained from the segmentation of the non-contrast images. The coarse-to-fine ML model generates an outcome of a fine masks (to be applied to the contrast image) in response to an input of a coarse mask. Alternatively, an adaptive threshold is learned and/or computed for creating fine calcification segmentations for the contrast images based on the non-contrast images. The adaptive threshold may separate between contrast (e.g., IV injected contrast) within the target anatomical structure (e.g., coronary artery, aorta, and the like) and calcifications within the target anatomical structure. The adaptive threshold may be learned, for example, by a machine learning model, trained on a training dataset of contrast images that also depict calcifications, using ground truth of a measure of HU (e.g., mean HU) for the anatomical structure within which the calcification is expected when there is contrast present and/or when there is no contrast present (e.g., the ascending aorta, coronary artery, carotid artery, and the like) and/or a ground truth measure of HU (e.g., mean HU) for the calcification. The machine learning model may be implemented, for example, as a deep neural network, and/or other implementations described herein.

The fine mask is applied to the contrast image. The calcification parameter(s) may be computed (as described herein) for the portion of the contrast image depicted by the applied fine mask. Alternatively or additionally, the calcification parameter(s) is computed for the portion of the non-contrast image depicted by the segmentation, which corresponds to the portion of the contrast image depicted by the applied fine mask.

At 210, one or more calcification parameters are determined for calcifications depicted within respective target anatomical structures.

Calcification parameter(s) may be determined for the non-contrast image, optionally within the segmented portion. Alternatively or additionally, calcification parameter(s) may be determined for the contrast image, optionally for the portion of the contrast image depicted by the applied fine mask.

Calcification parameters may be determined based on a measurement of measurement of contrast within the target anatomical structure, for example, measurement of contrast within the aorta, coronary artery, carotid artery, and the like. The contrast may be measured, for example, using the adaptive threshold described herein.

Optionally, when the target anatomical structure is a coronary artery, the calcification parameter is a coronary artery calcification (CAC) score (also referred to as coronary calcification score (CCS)), class, Agatston score, and/or risk category.

Calcification parameter(s) may be numerical values, individual numbers and/or ranges, which may be on a continuous and/or discrete scale, for example, where increasing numerical values represent increasing severity. Calcification parameter(s) may be categories, where categories may be arranged in terms of increasing severity, for example, mild, moderate, and severe.

Calcification parameters may be computed manually and/or automatically, for example, based on area of the calcification and/or intensity values of pixels depicting the calcification, such as Hounsfield Units (HU).

At 212, one or more other additional parameters may be accessed. The one or more additional parameters may be accessed per respective contrast enhanced image.

Optionally, the additional parameter(s) include one or more image parameters associated with the capture of the image, for example, settings of the imaging device (e.g., parameter settings of the CT scanner), kernel reconstruction, dose, scan protocol, single source vs dual source, ECG obtained during image acquisition, heart rate during image acquisition, administration of vasodilator prior to image acquisition, DICOM metadata, slice thickness, and increment.

Alternatively or additionally, the additional parameter(s) include one or more subject parameters associated with the subject depicted in the respective contrast enhanced image, for example, a subject demographic parameter, a medical history parameter, smoking history, family history, diabetes history, chronic kidney disease history, blood test values, cholesterol values, age (e.g., 30 and above, or other threshold) and a previous calcification parameter.

At 214, a training dataset is created.

Multiple records may be created, where each record includes a respective contrast enhanced image and optionally respective additional parameter(s) (e.g., respective image parameter(s) and/or respective subject parameters). Each record is labelled with the respective calcification parameter(s) as ground truth. Each record may further include ground truth of the computed fine mask, which delineates the calcification in the respective target anatomical structure. It is noted that records are not necessarily single units, but may represent a virtual aggregation of different data elements. The records are included in the training dataset.

Optionally, non-contrast medical images are excluded from the training dataset.

At 216 the ML model is trained on the training dataset. The ML model is trained for generating an outcome indicative of a target calcification parameter(s) for the target anatomical structure depicted in a target contrast enhanced medical image provided as input.

When the training dataset includes the fine masks computed for the contrast images, the ML model may be further trained for generating a target segmentation delineating calcification for the target contrast enhanced medical image.

The ML model may be implemented as a neural network based regression model, for example, when the classification parameter represents a scale of increasing severity. Alternatively or additionally, the ML model may be implemented as a classifier, such as a neural network based classifier, for example, when the classification parameter represents a classification category.

Optionally, the ML model is trained using a transfer learning approach. A baseline ML model is first trained on a baseline training dataset that includes the non-contrast medical images, each labelled with the ground truth label of the respective calcification parameter which was determined for that respective non-contrast medical image, as described herein. The ML model is then trained by further training the baseline ML model, using the transfer learning approach, on the training dataset that includes the contrast enhanced medical images, each labelled with ground truth label of the respective calcification parameter which were determined for the corresponding non-contrast medical image. The performance of the ML model may be increased by first training the baseline ML model on the non-contrast enhanced medical images, where calcification is "easier" for the ML model to learn to identify, since there is no contrast in the lumen that is visually similar to the calcification. The baseline model is then fine-tuned to learn to differentiate calcification from contrast by transfer learning on the contrast enhanced medical images. It is noted that the other parameters described herein may be included in the baseline training dataset.

Referring now back to FIG. 3, at 302, a target contrast enhanced image of a target subject is accessed. The target contrast image and target anatomical structure corresponds to the contrast images and target anatomical structures used in the training dataset for training the ML model, as described with reference to 202.

Optionally, the contrast enhanced image is a CTA image, and the target anatomical structure is a coronary artery.

At 304, one or more additional parameters may be accessed for the target contrast enhanced image, for example, image parameter(s) and/or subject parameters, as described herein.

At 306, the target contrast enhanced medical image depicting the target anatomical structure is fed into an ML model. The ML model is trained on a training dataset of records, each record including a respective contrast enhanced medical image(s) and optional additional parameter(s), labelled with a ground truth label of calcification parameter(s), for example, as described with reference to FIG. 2.

At 308, a target calcification parameter(s) is obtained for a target calcification depicted in the target anatomical structure as an outcome of the ML model. The target calcification parameter(s) may be, for example, a CAC score and/or class and/or Agatston value and/or risk category.

Alternatively or additionally, a fine mask delineating the target calcification depicted in the target anatomical structure is obtained as an outcome of the ML model.

At 310, the subject may be diagnosed and/or treated according to the target calcification parameter(s). The diagnosis may be done, for example, manually by a user (e.g., physician) and/or automatically by the executing code. Treatment may be administered to the subject, and/or instructions for treatment may be automatically generated and provided, for example, send to a mobile device, presented on a display, and/or printed on paper. For example, heart disease may be diagnosed when the CAC score and/or class is above a threshold. In another example, a treatment effective for preventing and/or reducing likelihood of heart disease is administered to the subject and/or instructions for administering the treatment are generated, when the CAC score and/or class is above a threshold. Exemplary treatments include weight loss, exercise regimen, change in diet, and cholesterol lowering medication(s).

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant machine learning models will be developed and the scope of the term machine learning model is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A computer-implemented method of training a machine learning (ML) model for identifying calcification in contrast enhanced medical images, comprising:
   for each set of a plurality of sets of sample medical images of a plurality of sample subjects depicting calcification within a target anatomical structure wherein each set includes at least one non-contrast medical image and at least one contrast enhanced medical image,
   correlating between calcifications depicted in the target anatomical structure of the at least one contrast enhanced image with corresponding calcifications depicted in the target anatomical structure of the at least one non-contrast medical image;
   computing at least one calcification parameter for calcification depicted in the respective target anatomical structure;
   labelling each contrast enhanced medical image with the at least one calcification parameter; and
   training the ML model on a training dataset that includes the plurality of contrast enhanced medical images of the plurality of sets, each labelled with ground truth label of a respective at least one calcification parameter, for generating an outcome indicative of a target at least one calcification parameter for calcification depicted in the target anatomical structure of a target contrast enhanced medical image provided as input;
   wherein the correlating comprises:
   registering between the target anatomical structure depicted in the at least one non-contrast medical image and the same corresponding target anatomical structure depicted in the at least one contrast enhanced medical image;
   segmenting calcification depicted in each respective non-contrast image;
   computing masks for respective segmented calcification of respective non-contrast images; and
   overlaying respective masks on the corresponding contrast images for delineating calcification depicted therein.

2. The computer-implemented method of claim 1, further comprising:
   training a coarse-to-fine ML model on a training dataset that includes coarse masks overlaid on the contrast images each labeled with a ground truth of a corresponding fine mask obtained from the segmentation of the non-contrast images, wherein the coarse-to-fine ML model generates an outcome of a fine masks (to be applied to the contrast image) in response to an input of a coarse mask; and
   feeding the respective mask into the coarse-to-fine ML model to obtain a fine mask; and
   placing the fine mask on the contrast image.

3. The computer-implemented method of claim 1, wherein the training dataset further comprises the masks computed for the contrast images, and wherein the ML model is further trained for generating a target segmentation delineating calcification for the target contrast enhanced medical image.

4. The computer-implemented method of claim 1, wherein training the ML model comprises:
   training a baseline ML model on a baseline training dataset that includes the plurality of non-contrast medical images of the plurality of sets, each labelled with the ground truth label of the respective at least one calcification parameter determined for the respective non-contrast medical image,
   wherein training the ML model comprises further training the baseline ML model on the training dataset that includes the plurality of contrast enhanced medical images of the plurality of sets, each labelled with ground truth label of the respective at least one calcification parameter determined for the corresponding non-contrast medical image.

5. The computer-implemented method of claim 1, further comprising:
   accessing a plurality of accessory non-contrast medical images without corresponding contrast enhanced medical images;
   determining, for each accessory non-contrast medical image, at least one calcification parameter for the respective calcification depicted in the target anatomical structure;
   synthesizing at least one contrast medical image from each accessory non-contrast medical image;
   labelling each synthesized contrast medical image with the ground truth label of the at least one calcification parameter determined for the non-contrast medical image used for synthesis of the synthesized contrast medical image; and
   including a plurality of labelled synthesized contrast medical images in the training dataset used for training the ML model.

6. The computer-implemented method of claim 1, further comprising analyzing the at least one contrast enhanced medical image to determine at least one specific contrast phase, and selecting contrast enhanced medical images designed as the at least one specific contrast phase, and excluding contrast enhanced medical images depicted non-selected contrast phases from further processing.

7. The computer-implemented method of claim 1, wherein the contrast enhanced image comprises a contrast-enhanced coronary computed tomography (CT) angiography (CTA) image, the non-contrast enhanced image comprises a non-contrast enhanced CT image, the target anatomical structure comprises a coronary artery, and the at least one calcification parameter comprises a coronary artery calcification (CAC) score and/or class and/or Agatston score and/or risk category.

8. The computer-implemented method of claim 1, further comprising:
   accessing, for each contrast enhance image, at least one image parameter;
   creating a plurality of records, each record including a respective contrast enhanced image, the respective at least one image parameter, and the ground truth label of the respective at least one calcification parameter; and
   including the plurality of records in the training dataset used to train the ML model.

9. The computer-implemented method of claim 1, wherein the at least one image parameter is selected from a group consisting of: kernel reconstruction, dose, scan protocol, single source vs dual source, ECG obtained during image acquisition, heart rate during image acquisition, administration of vasodilator prior to image acquisition, DICOM metadata, slice thickness, and increment.

10. The computer-implemented method of claim 1, further comprising:
   accessing, for each contrast enhance image, at least one subject parameter;
   creating a plurality of records, each record including a respective contrast enhanced image, the respective at least one subject parameter, and the ground truth label of the respective at least one calcification parameter; and including the plurality of records in the training dataset used to train the ML model.

11. The computer-implemented method of claim 10, wherein the at least one subject parameter is selected from a group consisting of: a subject demographic parameter, a medical history parameter, smoking history, family history, diabetes history, chronic kidney disease history, blood test values, cholesterol values, a previous calcification parameter, and age over a threshold.

12. A computer-implemented method of training a machine learning (ML) model for identifying calcification in contrast enhanced medical images, comprising:

for each set of a plurality of sets of sample medical images of a plurality of sample subjects depicting calcification within a target anatomical structure wherein each set includes at least one non-contrast medical image and at least one contrast enhanced medical image, correlating between calcifications depicted in the target anatomical structure of the at least one contrast enhanced image with corresponding calcifications depicted in the target anatomical structure of the at least one non-contrast medical image;

computing at least one calcification parameter for calcification depicted in the respective target anatomical structure;

labelling each contrast enhanced medical image with the at least one calcification parameter; and excluding non-contrast medical images from a training dataset that includes the plurality of contrast enhanced medical images of the plurality of sets, each labelled with ground truth label of a respective at least one calcification parameter;

training the ML model on the training dataset for generating an outcome indicative of a target at least one calcification parameter for calcification depicted in the target anatomical structure of a target contrast enhanced medical image provided as input.

13. The computer-implemented method of claim 12, wherein the ML model is implemented as a neural network based regression model.

14. The computer-implemented method of claim 12, wherein the medical image includes slices extracted from a CT scan.

15. A computing device for training a machine learning (ML) model for identifying calcification, comprising:

at least one hardware processor executing a code for:

for each set of a plurality of sets of sample medical images of a plurality of sample subjects depicting calcification within a target anatomical structure wherein each set includes at least one non-contrast medical image and at least one contrast enhanced medical image, correlating between calcifications depicted in the target anatomical structure of the at least one contrast enhanced image with corresponding calcifications depicted in the target anatomical structure of the at least one non-contrast medical image;

computing at least one calcification parameter for calcification depicted in the respective target anatomical structure;

labelling each contrast enhanced medical image with the at least one calcification parameter; and training the ML model on a training dataset that includes the plurality of contrast enhanced medical images of the plurality of sets, each labelled with ground truth label of a respective at least one calcification parameter, for generating an outcome indicative of a target at least one calcification parameter for calcification depicted in the target anatomical structure of a target contrast enhanced medical image provided as input;

wherein the correlating comprises:

registering between the target anatomical structure depicted in the at least one non-contrast medical image and the same corresponding target anatomical structure depicted in the at least one contrast enhanced medical image;

segmenting calcification depicted in each respective non-contrast image;

computing masks for respective segmented calcification of respective non-contrast images; and overlaying respective masks on the corresponding contrast images for delineating calcification depicted therein.

* * * * *